United States Patent [19]

Kannagi et al.

[11] Patent Number: 4,885,358

[45] Date of Patent: Dec. 5, 1989

[54] MONOCLONAL ANTIBODIES SPECIFIC FOR SYNTHETIC GLYCOSPHINGOLIPIDS HAVING ABNORMAL BRANCHED STRUCTURE

[75] Inventors: Reiji Kannagi, Kyoto; Katsuyoshi Shigeta, Suita; Yukishige Ito, Tokyo; Yoshiko Kirihata, Kyoto; Tomoya Ogawa, Musashino, all of Japan

[73] Assignee: MECT Corporation, Tokyo, Japan

[21] Appl. No.: 13,536

[22] Filed: Feb. 11, 1987

[51] Int. Cl.$^4$ ............... A61K 39/395; C07K 15/14
[52] U.S. Cl. ............... 530/387; 530/806; 530/808; 530/828; 424/85.8; 435/240.27; 435/172.2
[58] Field of Search ............... 530/387, 806, 808, 828; 435/68, 172.2, 240.27; 935/104; 424/85.8

[56] References Cited

PUBLICATIONS

Brodin et al., Eur. J. Immunol, 16, 951–6, (1986).
Bremer et al., J. Biol. Chem., 259(23), 14773–7, (1984).
Fukushi et al., J. Biol. Chem., 259(16), 10511–17, (1984).
Fukushi et al., Canc. Res., 45, 3711–17, (1985).
Bast et al., N. Eng. J. Med., 309(15), 883–7, (1983).
Huang et al., Arch. Bioch. Biophys., 220(1), 381–20, (1983).
Kannagi et al., Canc. Res., 46, 2619–26, (1986).
Koiki, K., Nakahara, Y., and Ogawa, T., (1984), Glycoconjugate J. 1, 107–109.
Ogawa, T., and Sugimoto, M., (1985), Carbohydr. Res. 135, C5–C9.
Paulsen, H., (1982), Angew. Chem. Int. Ed. Engl., 21, 155–224.
Kannagi, R., and Hakomori, S., (1986), Handbook of Experimental Immunology, 4, 117.1–117.20.
Ogawa, T., and Sugimoto, M., (1984), Carbohydr. Res., 128, C1–C4.
C. Galanos., O. Luderitz., and O. Westphal., (1971), Eur. J. Biochem., 24, 116–122.
Young, Jr., W., MacDonald, E. M. S., Nowinski, R. C., and Hakomori, S., (1979), J. Exp. Med., 150, 1008–1009.
G. Kohler., and C. Milstein, (1976), Eur. J. Immunol., 6, 511–519.
G. Kohler., and C. Milstein., (1975), Nature, 256, 495–497.
Cancer Research, vol. 45, Jun. 1985, pp. 2405–2414.
Cancer Research, vol. 43, Oct. 1983, pp. 4997–5005.
Handbook of Experimental Immunology, vol. 4, pp. 1–4.
Nature, vol. 314, Mar. 1985, pp. 53–57.
The Journal of Biological Chemistry, vol. 259, No. 9, May 1984, pp. 6008–6012.
The Journal of Biological Chemistry, vol. 259, No. 13, Jul. 1984, pp. 8444–8451.
JNCI, vol. 71, No. 2, Aug. 1983, pp. 231–251.
Molecular Immunology, vol. 21, No. 10, 1984, pp. 877–882.
J. Exp. Med., vol. 150, Oct. 1979, pp. 1008–1019.

*Primary Examiner*—Lester L. Lee
*Assistant Examiner*—Jeff Kushan
*Attorney, Agent, or Firm*—Oblon, Spivak, McClelland, Maier & Neustadt

[57] ABSTRACT

Hybridomas which produce monoclonal antibodies specific to an abnormal branched determinant of a synthetic glycolipid antigen and methods of use of the monoclonal antibodies.

10 Claims, 14 Drawing Sheets

MONOSACCHARIDE DONORS (3+8 STEPS)

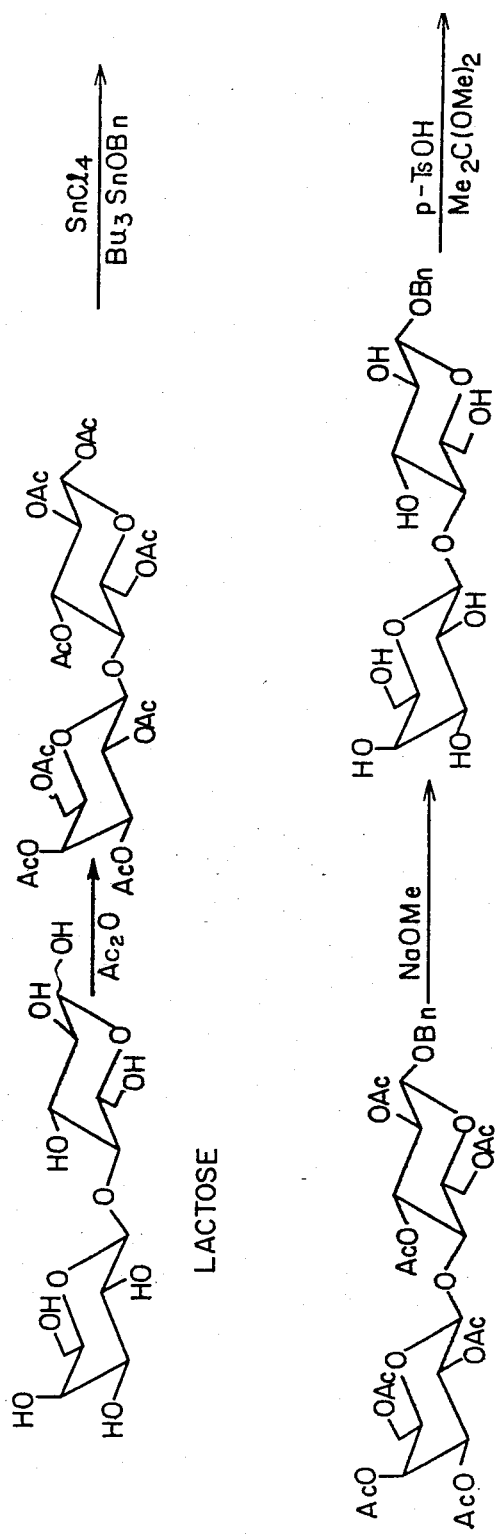

TETRASACCHARIDE DONOR (8 STEPS)

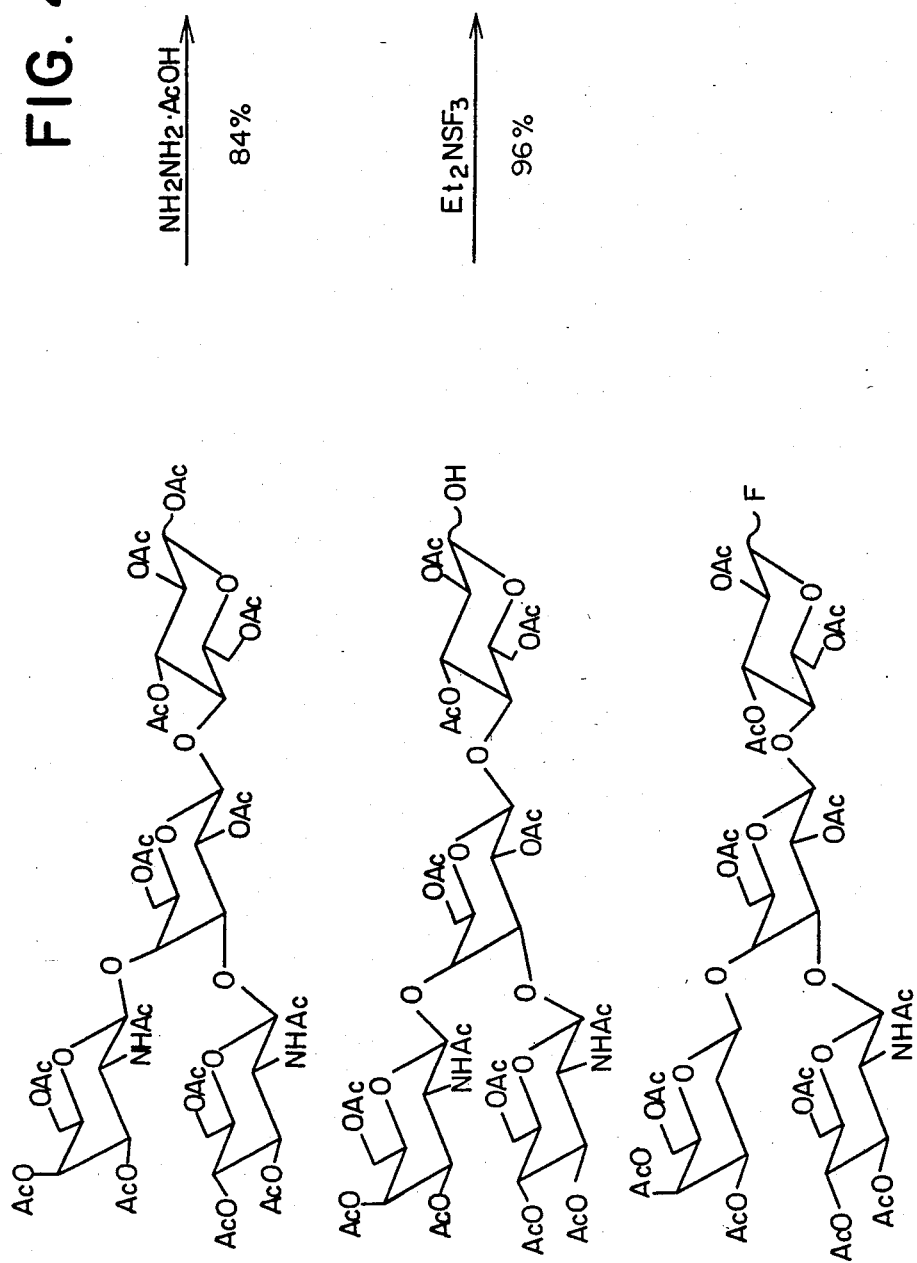
FIG. 4 CONT2.

MONOBENZOYL CERAMIDE (15 STEPS)

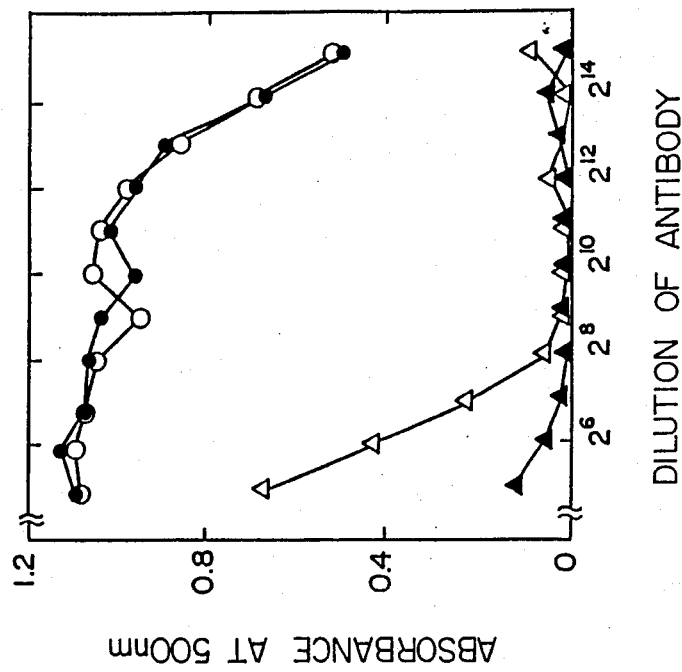
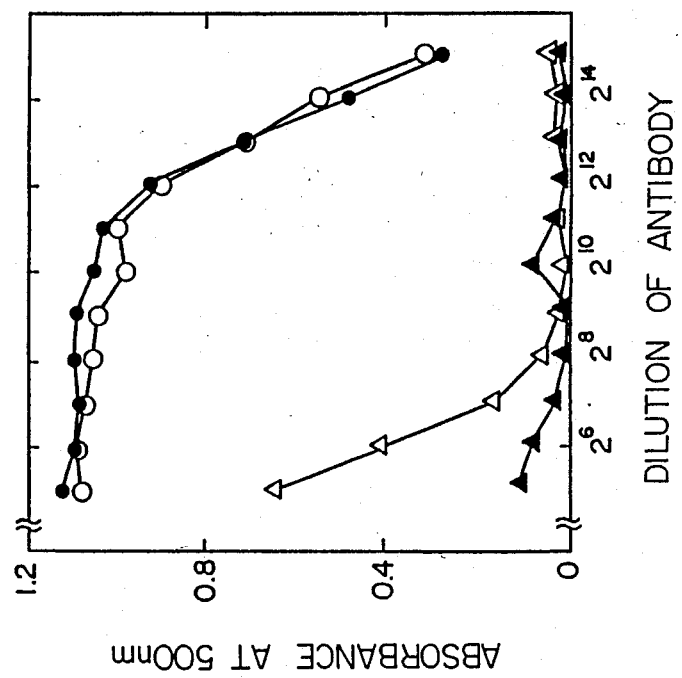

MONOCLONAL ANTIBODIES SPECIFIC FOR SYNTHETIC GLYCOSPHINGOLIPIDS HAVING ABNORMAL BRANCHED STRUCTURE

BACKGROUND OF THE INVENTION

1. Field of the Invention

The present invention is directed to hybridoma cell lines which produce monoclonal antibodies specific for glycosphingolipids and to the monoclonal antibodies produced by the hybridomas. More particularly, the invention is directed to hybridomas which produce monoclonal antibodies recognizing an abnormal branching structure in a glycosphingolipid. The invention is further directed to a method of chemically synthesizing a glycosphingolipid, and a method for detecting a cancer-associated glycosphingolipid using the monoclonal antibodies of the invention.

2. Description of the Related Art

In 1975, Kohler and Millstein introduced a procedure for the production of monoclonal antibodies using hybrid cells (hybridomas) which allows the production of almost unlimited quantities of antibodies of precise and reproducible specificity. Before that time, conventional antisera which were produced by immunizing animals with tumor cells or other antigens were found to contain a wide variety of different antibodies which differed in their specificity and properties. On the other hand, hybridomas produce a single antibody with uniform characteristics. The Kohler-Millstein procedure entails the fusion of spleen cells from an immunized animal with an immortal myeloma cell line. From the fused cells, known as hybridomas, clones are selected that produce antibody of the desired specificity. Each clone continues to produce only that one antibody. As hybridoma cells can be cultured indefinitely or stored frozen in liquid nitrogen, a constant supply of that particular antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant. Not all of the hybridoma clones which result from fusing neoplastic cells with antibody producing cells are specific for the desired foreign substance or antigen because many of the hybridomas will make antibodies which the innoculated animal has produced to react with other foreign substances. Even antibodies against the subject antigen will differ from clone to clone because antibodies produced by different cells may react with different antigenic determinants of the same molecule. Thus, it is impossible to predict in advance which particular portion of the antigen molecule a particular monoclonal antibody might recognize. Many of the techniques for producing monoclonal antibodies and hybridomas are now routine, as evidenced by the recent book "Monoclonal Hybridoma Antibodies: Techniques and Applications" (edited by John G. Hurrell, 1983), which is hereby incorporated by reference.

The present invention is directed in particular to monoclonal antibodies (and hybridomas producing them), which recognize certain carbohydrate antigens associated with cancer. Carbohydrate antigens have been shown to be important cancer-associated antigens by several researchers. See Hakomori, S. & Kannagi, R., J. Natl. Cancer Inst. 71, 231-251; Feizi, T., Nature 314, 53-54, 1985; Hakomori, S., Cancer Res. 45, 2405-2414, 1985; and Magnani, J. L., Biochem. Soc. Trans. 12, 543-545, 1984, each of which is incorporated herein by reference. Several monoclonal antibodies raised against cancer cells have been shown to recognize abnormal cell surface carbohydrate antigens carried by glycolipids, or, less frequently, by glycoproteins. Some of these antibodies are already applied to measure the presence of antigens in the sera of patients with various cancers. See Koprowski, H. et al., Science 212, 53-55, 1979; Metzger, et al, Cancer Res. 42, 601-608, 1982; Bast, R. et al, N. Eng. J. Med. 309, 883-887, 1983.

More recently, cancer-associated glycolipid antigens extracted and purified from various human tumor cells have been directly utilized for immunization of mice, and several monoclonal antibodies useful for the detection of human cancer have been established. See Hakomori, S. et al, J. Biol. Chem. 259, 4681-4685, 1984; Fukushi, Y. et al, J. Biol. Chem. 259, 10511-10517, 1984; Fukushi, et al, Cancer Res. 45, 3711-3717, 1985; and Kannagi et al., Cancer Res. 46, 2619-2626, 1986.

In spite of the above successes in producing antibodies to glycolipid antigens, some cancer-associated glycolipids are very minor membrane components, and frequently it is not easy to purify them from natural sources in a satisfactory amount for the preparation of monoclonal antibodies. Even though progress has been made in the methodology for purification of glycolipid antigens, the small amounts of these materials has rendered monoclonal antibodies to them impossible to obtain in some instances. In such cases, it would be better to obtain the glycolipid antigen through chemical synthesis, and then to obtain monoclonal antibodies directed to the synthetic antigens. However, the chemical synthesis of these glycolipids is greatly complicated by their stringent structural requirements, such as unusual branching structures, stereochemical configurations, large molecular weights and other complex structural features. Moreover, synthetic schemes are often not feasible because of low yields in required reactions, and the long reaction sequences involved.

Another complicating factor in obtaining monoclonal antibodies specific to cancer-associated glycolipids is that the desired monoclonals must recognize a particular feature of the glycolipid such as an abnormal branching portion. At the same time, the monoclonals must not cross-react with portions of the antigen molecule which are present on the individual segments of the assembled antigen molecule.

In view of the above difficulties, there continues to remain a need for new methods of obtaining monoclonal antibodies to rare antigens, such as cancer-associated glycolipid antigens, and for the monoclonal antibodies themselves.

SUMMARY OF THE INVENTION

Accordingly, it is an object of the present invention to provide monoclonal antibodies which recognize abnormal branching structures in cancer-associated glycosphingolipids;

It is yet another object of the present invention to provide monoclonal antibodies capable of recognizing the cancer-associated lactoganglioseries glycolipid, which is the abnormal branched hybrid molecule of asialo $GM_2$ ($Gg_3$) and amino CTH ($LC_3$), said monoclonal antibodies not cross-reacting with the unbranched smaller portions of the glycolipid, such as asialo GM2 and pure amino CTH;

It is yet another object of the present invention to provide hybridoma cells capable of producing monoclonal antibodies according to the invention;

It is yet another object of the present invention to provide a method for detecting the presence of branched structures of cancer-associated glycolipid antigens;

It is yet another object of the present invention to provide a method of synthesizing the cancer-associated lactoganglioseries glycolipid.

The above objects and others as will become hereinafter more apparent, have been accomplished by the present invention, which provides a synthetic-method for preparing the cancer-associated lactoganglioseries glycolipid and hybridomas which produce monoclonal antibodies recognizing the branched-structure of this glycolipid.

Figure 1:
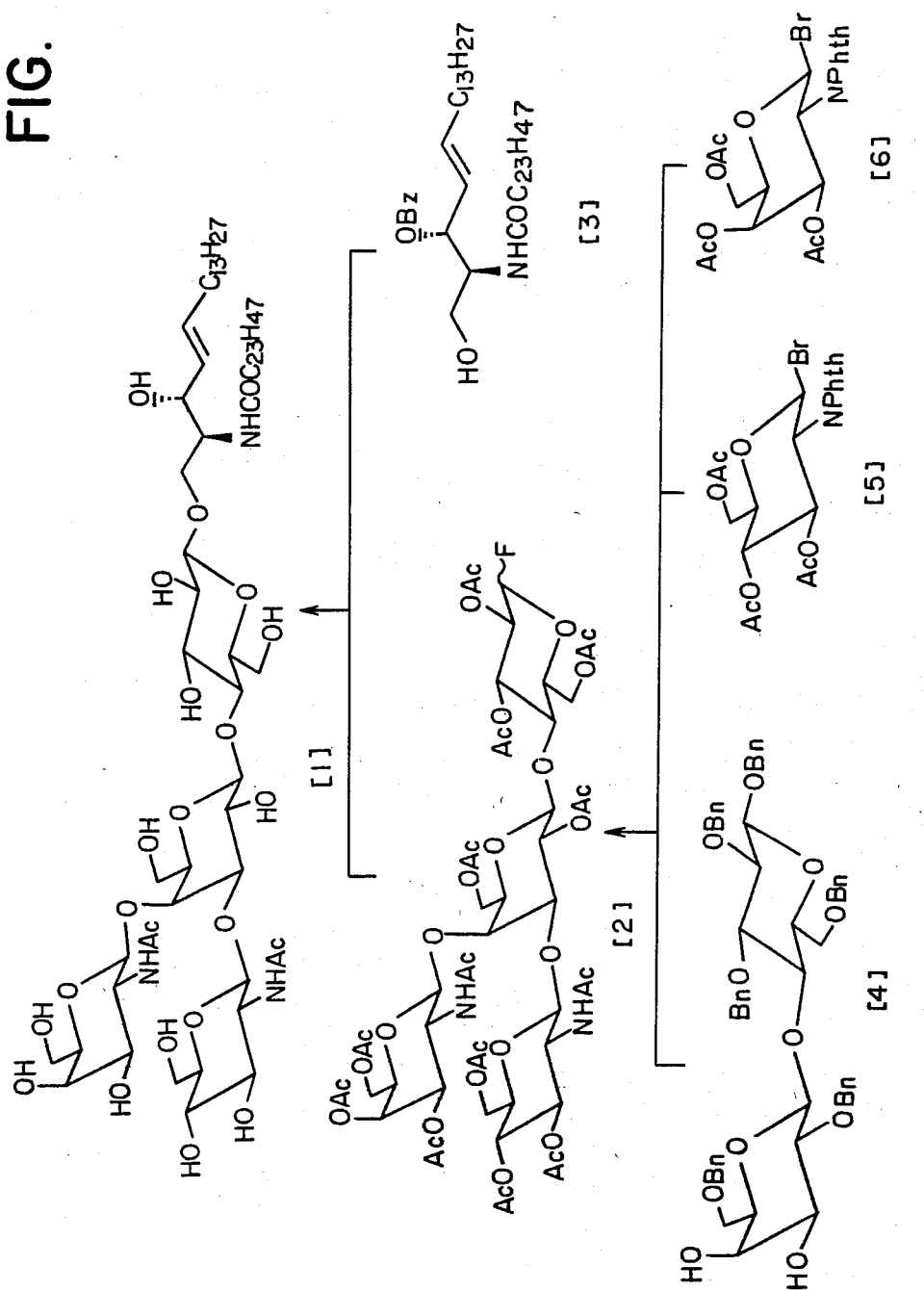
FIG. 1—Overall scheme for the synthesis of a lactoganglioseries glycolipid. Bn, benzyl; Phth, phthaloyl; Bz, benzoyl; Ac, acetyl.
Figure 2:
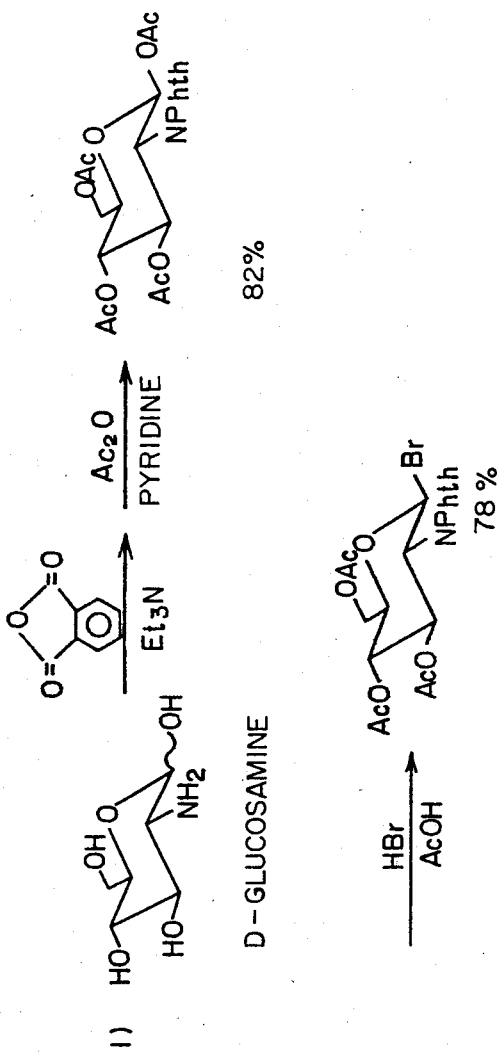
FIGS. 2–6—Specific reaction steps for synthesizing the lactoganglioseries glycolipid.
Figure 2:
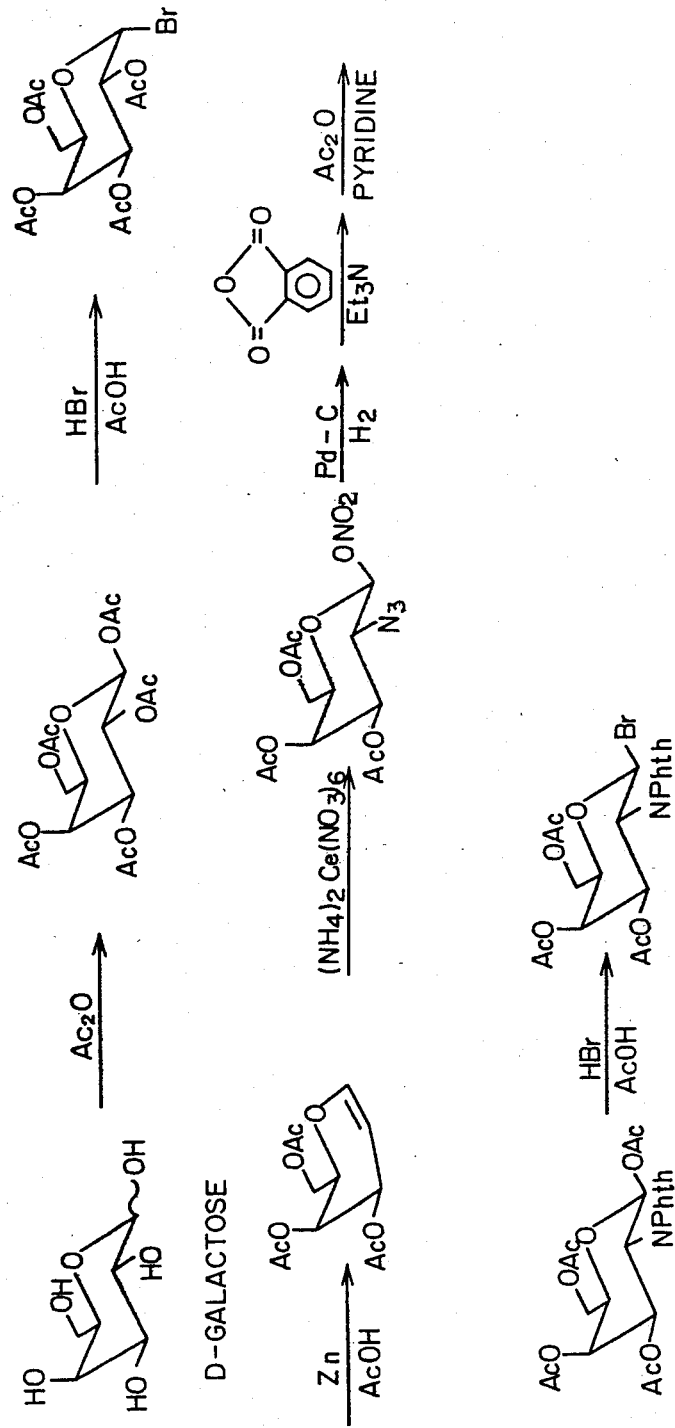
Figure 3:
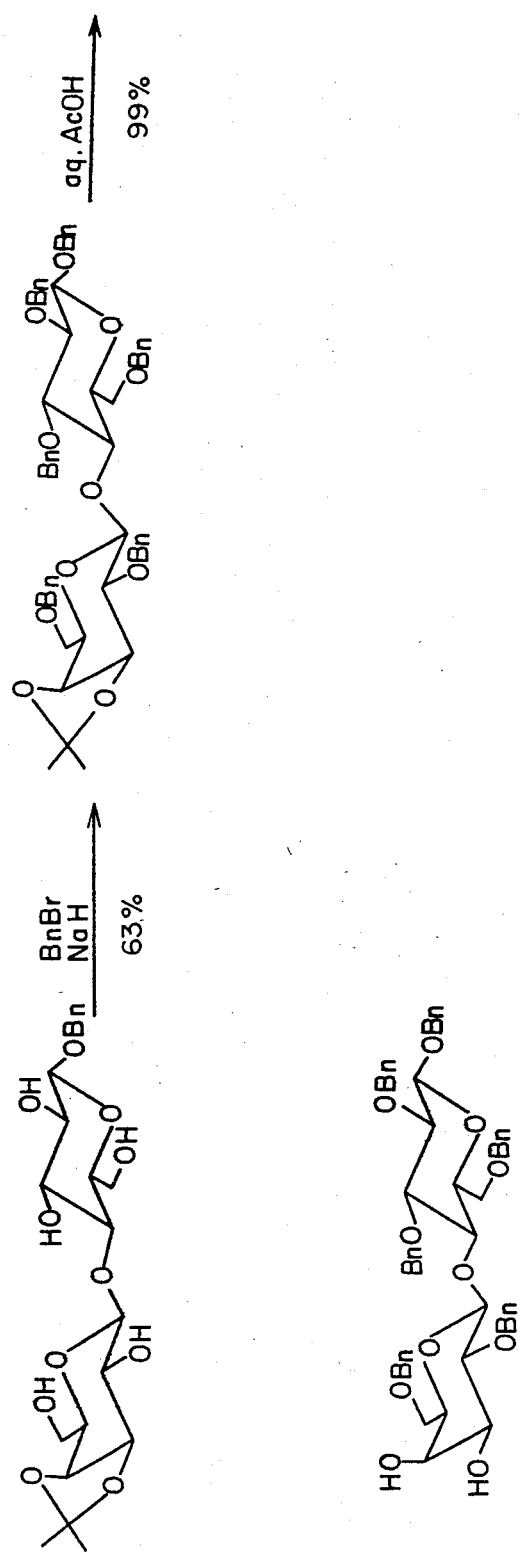
Figure 4:
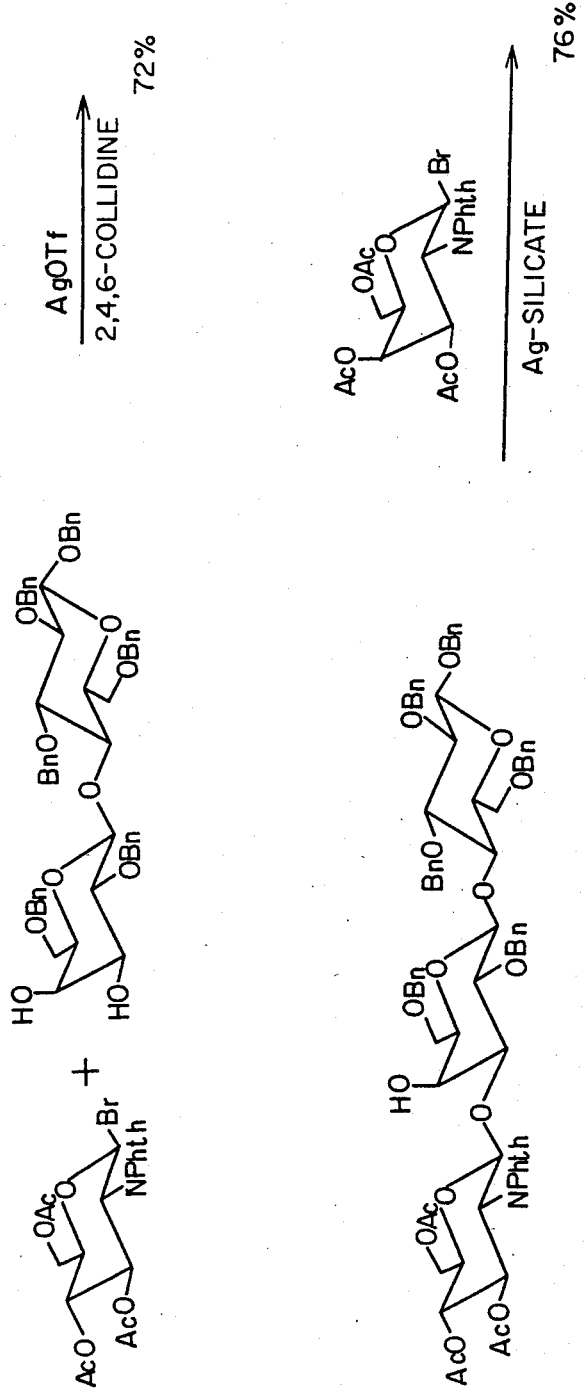
Figure 4:
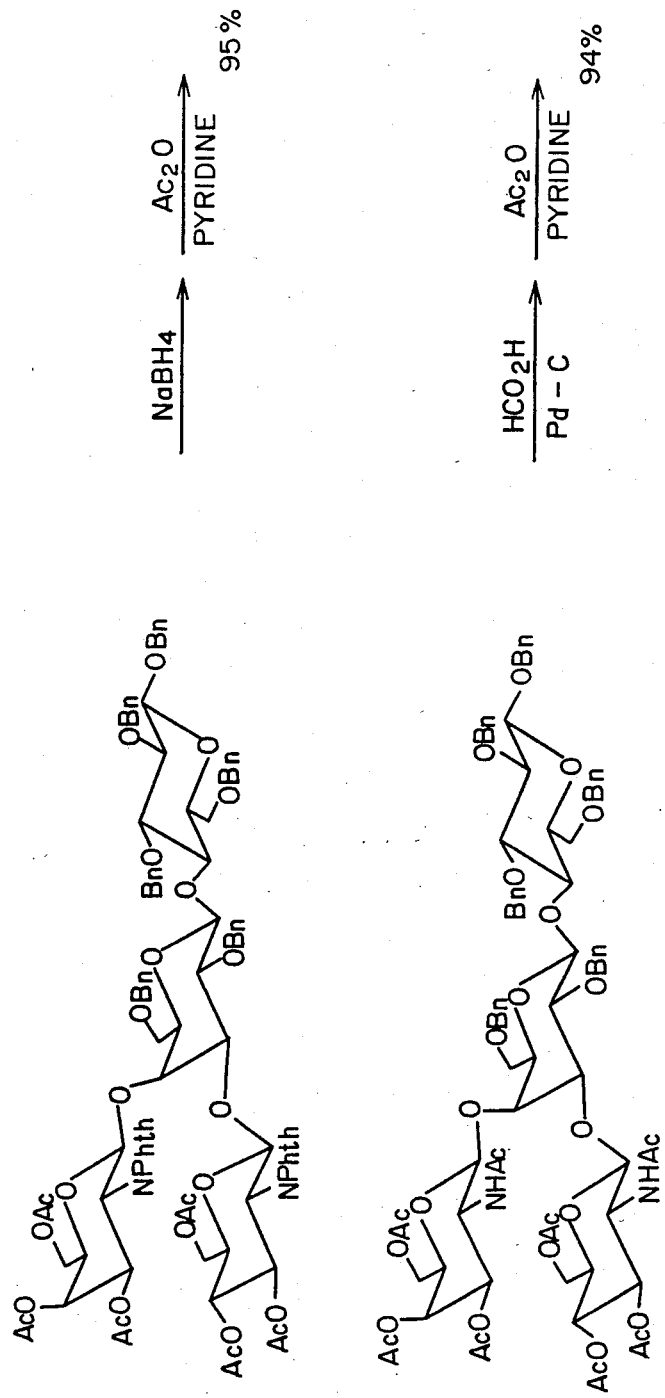
Figure 5:
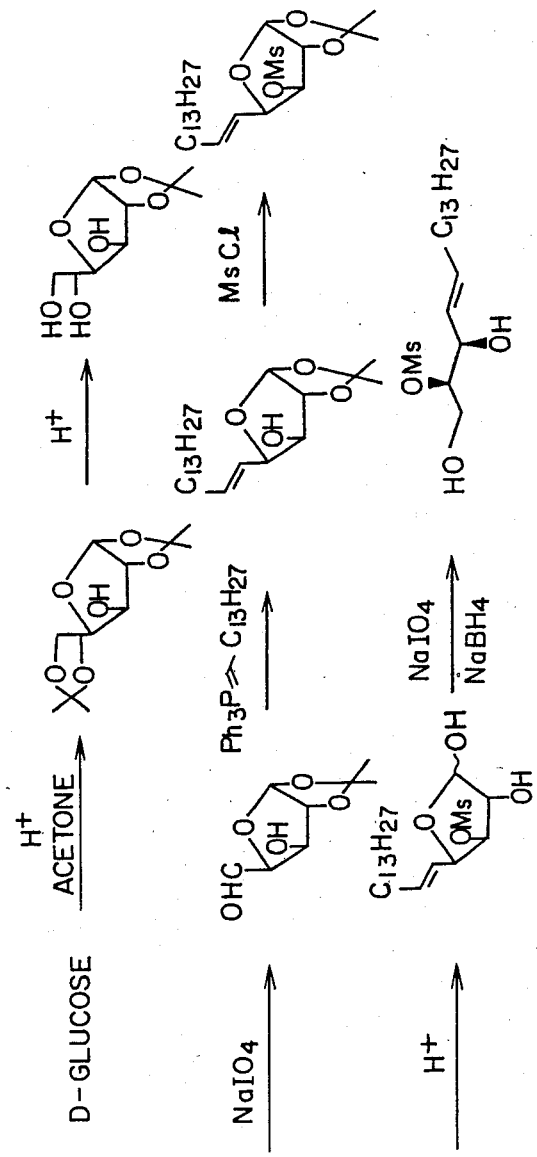
Figure 5:
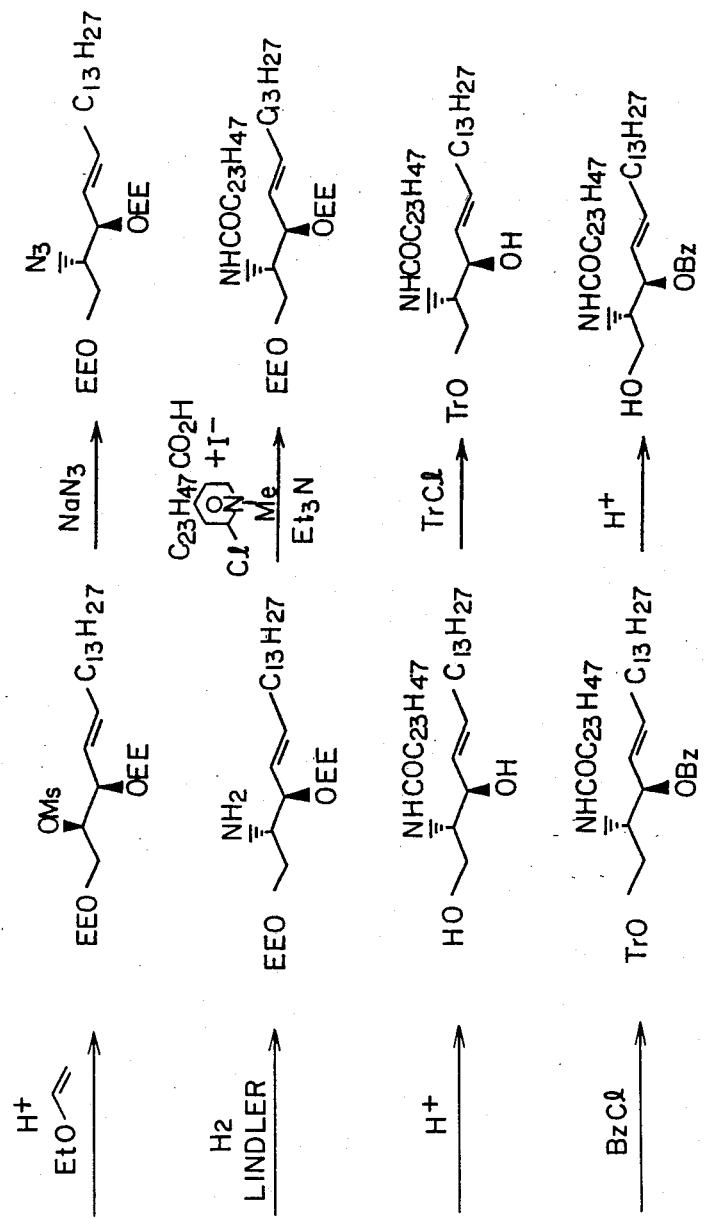
Figure 6:
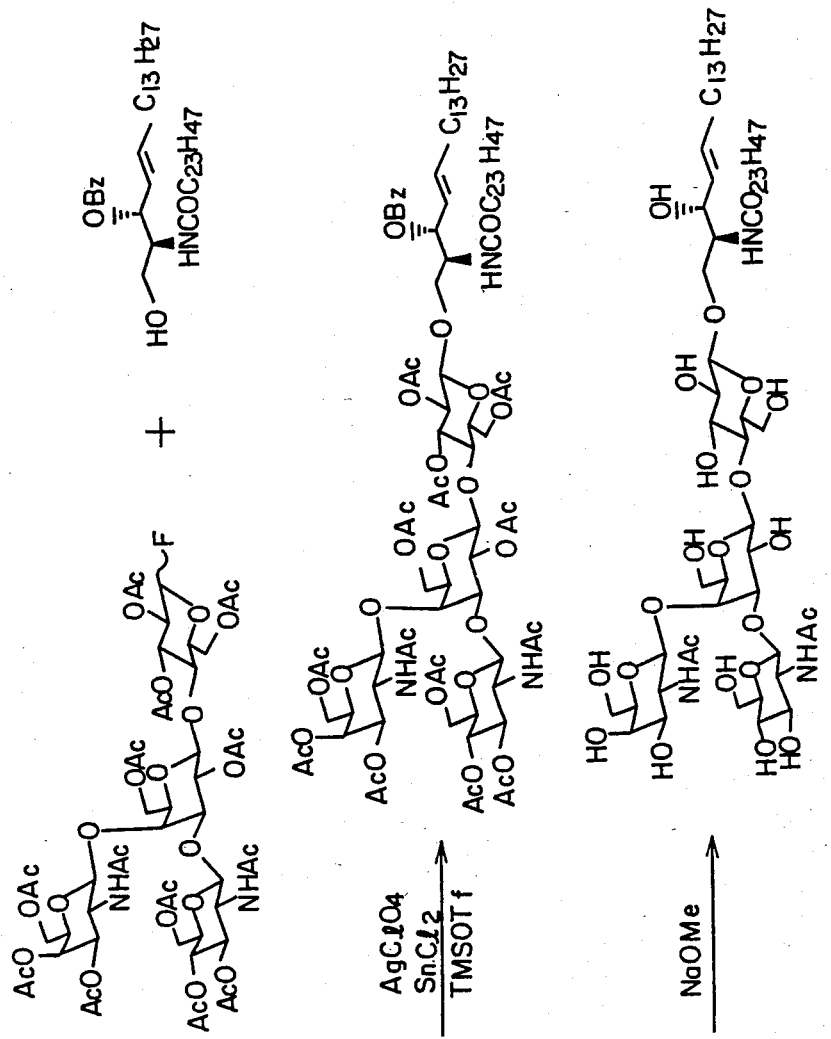
Figure 7A:
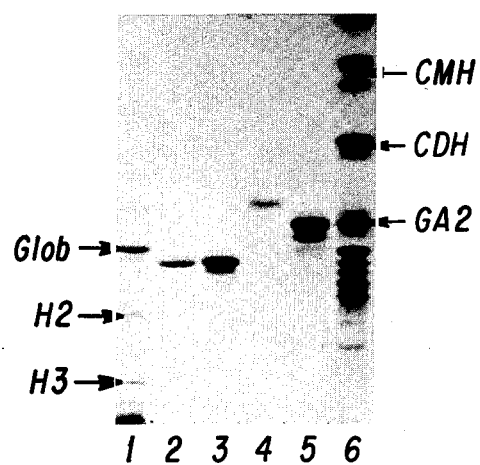
FIG. 7—Specificity of the monoclonal antibody YI328-18 and YI328-51 as ascertained by TLC staining.
Figure 7B:
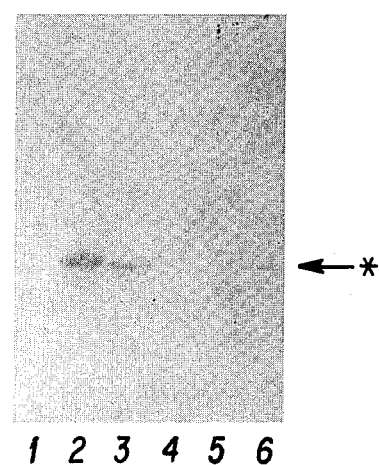
Figure 7C:
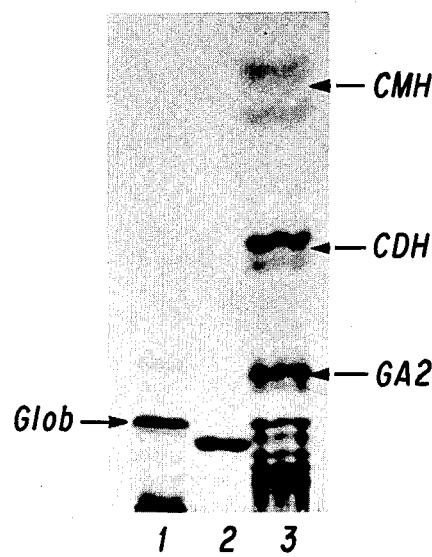
Figure 7D:
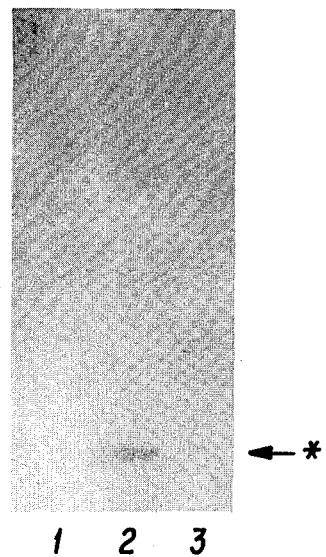

(a) Orcinol—$H_2SO_4$ reaction of TLC, and (b) immunostaining of the same TLC as in (a) with the monoclonal YI328-18 antibody. Lane 1, neutral glycolipid mixture prepared from type O human erythrocytes; lane 2, the synthetic lactoganglioseries glycolipid; lane 3, the lactoganglioseries glycolipid purified from undifferentiated M1 cells; lane 4, pure amino ceramide trihexoside (CTH); lane 5, pure asialo GM2; lane 6, neutral glycolipid mixture prepared one of the undifferentiated M1 cell clones, n-D6. See Kannagi et al, Proc. Natl. Acad. Sci. USA 80, 2844–2848, 1983. An arrow with an asterisk in (b) shows the TLC mobility of the lactoganglioseries glycolipid. It is notable that only the lactoganglioseries glycolipid in lanes 2, 3 and 6 shows positive staining by TLC immunostaining.

(c) Orcinol-$H_2SO_4$ reaction of TLC, and (d), immunostaining of the same TLC as in (c) with the monoclonal YI328-51 antibody. Lane 1, neutral glycolipid mixture prepared from type O human erythrocytes; lane 2, the synthetic lactoganglioseries glycolipid; lane 3, neutral glycolipid mixture prepared from n-D6. A positive staining is observed in lanes 2 and 3 as indicated by an arrow with an asterisk in (d). Reactivity of YI328-51 antibody towards the lactoganglioseries glycolipid purified from a natural source, and pure amino CTH or asialo GM2 was essentially the same as that of YI328-18 antibody (not shown).

Abbreviations: Glob, globoside (Gb4); GA2, asialo GM2 (Gg3) CDH (LacCer), ceramide dihexoside or lactosylceramide. CMH, ceramide monohexoside.

FIG. 8—Specificity of the monoclonal antibody YI328-18 (a) and YI328-51 (b) ascertained by solid-phase enzyme immunoassay. (○), Synthetic lactoganglioseries glycolipid; (●), lactoganglioseries glycolipid purified from undifferentiated M1 cells; (△), amino CTH; and (▲) asialo GM2 were used as antigens.

Figures 9A, 9B:
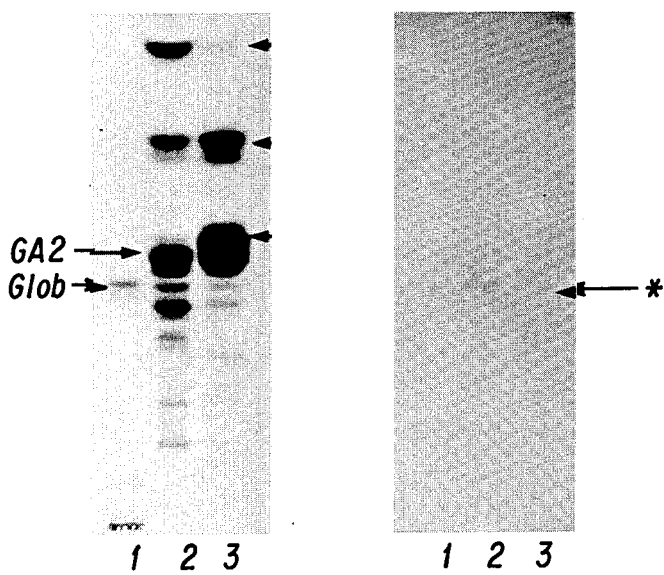

FIG. 9—Differentiation-dependent decrease of the lactoganglioseries hybrid glycolipid as ascertained by TLC staining.

(a) Orcinol-$H_2SO_4$ reaction of TLC, and (b), immunostaining of the same TLC as in (a) with the monoclonal YI328-18 antibody. Lane 1, neutral glycolipid mixture prepared from type O human erythrocytes; lane 2, neutral glycolipid mixture prepared from undifferentiated M1 cells; lane 3, neutral glycolipid mixture prepared from differentiated M1 cells. A positively stained band is observed only in lane 2, the TLC mobility of which is shown by an arrow with an asterisk in (b). The TLC mobility of the lactoganglioseries glycolipid coincides with that of paragloboside, which migrates just beneath the globoside.

Abbreviations: Glob, globoside (Gb4); GA2, asialo GM2 (Gg3).

DESCRIPTION OF THE PREFERRED EMBODIMENTS

A particularly preferred branched glycolipid according to the present invention is the lactoganglioseries glycolipid shown in FIG. 1. Other, structurally related analogues of the glycolipid of FIG. 1 could also be useful for purposes of the present invention. In particular, as long as the branched portion of the molecule remains the same, substitutions and modifications at other portions of the molecule are possible. For example, distal hydroxyl groups may be replaced by amino groups. Also, the $C_{13}$ and $C_{23}$ carbon chains may contain, e.g., up to 5 additional or fewer carbon atoms, and multiple unsaturations may be present in, e.g., these carbon chains.

The lactoganglioseries glycolipid of FIG. 1 is a minor glycolipid component of undifferentiated cells. See Kannagi, R. et al., J. Biol. Chem. 257, 14865–74 (1982). A connection between the presence of this type of glycolipid and cellular differentiation has been observed. Cultured murine leukemia cells, M1, have an ability to differentiate into mature macrophage-like cells when cultured with appropriate inducers such as LPG or conditioned medium. See Ichikawa, J., J. Cell Physiol. 74, 223–224, 1969; Kannagi et al., Biochim. Biophys. Acta 712, 161–168, 1982; Kanangi et al, Biochem. Biophys. Res. Comm. 105, 1964–171, 1982. During the course of differentiation, cellular glycolipid composition undergoes several stages of remarkable changes (Kannagi, R. et al., Proc. Natl. Acad. Sci. USA 80, 2844–2848 (1983)). The most undifferentiated type of cells contain mainly ganglioseries glycolipids and a small amount of lactoseries glycolipids. A considerable increase of lactoseries glycolipids and a concomitant decrease of ganglioseries glycolipids are noted at the middle stage of differentiation; and finally, the synthesis of a globoseries glycolipid (CTH, Gb3) is initiated. This glycolipid comprises up to 47% of total cellular glycolipid at the end of the differentiation stage.

The carbohydrate structure of the lactoganglioseries glycolipid shown in FIG. 1 is highly abnormal in that a ganglioseries structure (asialo GM2 structure) and a lactoseries structure (amino CTH structure) co-exist in the same molecule, mediated through the abnormal branching structure at II-galactose. By abnormal branching is meant a connection other than a typical 1→4 connection, such as 1→3 connection. The abbreviated structure of this glycolipid is as follows:

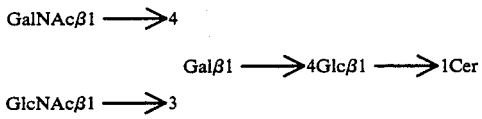

The elemental unbranched structures such as asialo GM$_2$, amino CTH, and, of course, CDH are very common glycolipids, which are found in some normal tissues as well as tumor tissues, and can easily be purified in relatively large amounts. Monoclonal antibodies which recognize these simple glycolipids have already been reported. See Young, W. W. Jr. et al, J. Exp. Med. 150, 1008–1019, 1979; Symington, F. W. et al., J. Biol. Chem. 159, 6008–6012, 1984; and Symington, F. W. et al, Mol. Immunol. 21, 877–882, 1984. The glycolipid is regarded as a tumor-associated glycolipid because of its abnormal structure as well as the finding that the content of this glycolipid diminishes during the course of differentiation. In particular, the lactoganglioseries glycolipid of this invention (see FIG. 1) is associated with leukemia. See Kannagi, R. et al. J. Biol. Chem. 259, 8444–8451, which is hereby incorporated by reference.

The patterns of cancer-associated change of carbohydrate structure include (1) abnormal elongation or shortening, (2) abnormal repetition, and (3) abnormal branching. Since the lactoganglioseries glycolipid is regarded as a typical example representing cancer-associated abnormal branching of carbohydrates, it has been of interest to see whether or not a similar abnormal branching structure is present in other murine and human leukemia cells as well as in other cancer tissues by utilizing a specific monoclonal antibody.

However, the glycolipid is a very minor component and it has been difficult to obtain a sufficient amount of pure glycolipid for the preparation of monoclonal antibodies.

For such a purpose the glycolipid must be synthesized strictly in a stereo- and regio-controlled manner. If undesirable anomeric or positional isomers or other contaminants are mixed in the final synthetic glycolipid preparations, these could be highly immunogenic and could interfere with the preparation of monoclonal antibodies specific for the original glycolipid.

The method developed according to the present invention involves chemical synthesis by organic chemistry techniques not involving enzymatic conversions using a lactose unit, a ceramide unit and hexosamine donors as synthetic units (synthons). The steps involved in the synthetic scheme to produce this particular lactoganglioseries glycolipid are described in the examples herein and are depicted schematically in FIGS. 1-6.

Additional specific aspects of the types of reactions outlined in the Figures may be found in published articles such as the following: R. U. Lemieux, T. Takeda, B. Y. Chung, ACS Sympo. Ser., 39, 90 (1976); R. U. Lemieux, R. M. Ratcliff, Can. J. Chem., 57, 1244 (1979); T. Ogawa, M. Sugimoto, Carbohydr. Res., 135 C5 (1985); Y. Ito, M. Sugimoto, S. Gato, T. Ogawa, Tetrahedron Lett., 27, 4753 (1986); K. Koike, Y. Nakahara, T. Ogawa, Glycoconjugate J., 1, 107 (1984); and M. Sugimoto, T. Ogawa, Glycoconjugate J., 2, 5 (1985).

After obtaining the chemically synthesized glycolipid, it was used as an antigen in order to produce monoclonal antibodies using techniques such as those disclosed in John G. Hurrell, "Monoclonal Hybridoma Antibodies: Techniques and Applications", CRC 1983.

Two hybridomas of particular interest were obtained, YI328-18 and YI328-51. Both of these produce IgG$_3$ isotype antibodies which specifically recognize the abnormal branching structure of lactoganglioseries glycolipid antigen, and have almost no cross-reactivity with smaller unbranched segments of the antigen molecule. Cross-reactivity can be determined according to a method as outlined in the examples herein. Cross-reactivity of from 0% to 1% towards the unbranched elementary structures such as asialo GM$_2$ or amino CTH is preferred. Particularly preferred is a cross-reactivity towards unbranched elementary structures of less than 0.78%. These hybridomas have been deposited at the American Type Culture Collection (ATCC), 12301 Parklawn Drive, Rockville, Md. 20852. The hybridoma YI328-18 is ATCC No. HB 9306 and the hybridoma YI328-51 is ATCC No. HB 9307. Both have deposit dates of Oct. 24, 1986.

According to the present invention, it is now possible to use synthetic glycolipids as immunogens to enable the production of specific monoclonal antibodies directed to various cancer-associated glycolipids which are very minor components, or to obtain monoclonal antibodies which are directed to putative cancer-associated glycolipids which can be artificially designed.

The results in the examples herein clearly show that the obtained monoclonal antibodies specifically recognize the designated glycolipid, as evidenced by their equal reactivity with the synthetic lactoganglioseries glycolipid and the naturally-occuring glycolipid isolated from M1 cells. This shows that the synthesized glycolipid is pure enough not only in a chemical sense, but also in terms of its immunological grade.

Most of the known anticarbohydrate monoclonal antibodies belong to the IgM class of antibodies. However, surprisingly, the two antibodies obtained in the present study both belong to the IgG class, which is unusual for an anticarbohydrate antibody. Antiasialo GM$_2$, anti-amino CTH and anti-CDH antibodies are mainly of the IgM class. See Young, W. W. Jr., McDonald, E. M. S., Nowinski, R. C. & Hakomori, D. (1979) J. Exp. Med. 150, 1008–1019; Symington, F. W., Bernstein, I. D. & Hakomori, S. (1984) J. Biol. Chem. 159, 6008–6012; and Symington, F. W., Fenderson, B. A. & Hakomori, S. (1984) Mol. Immunol. 21, 877–882. The present results imply that the abnormal branching structure can elicit a preferential IgG response.

The present results collectively indicate that it is quite feasible to synthesize cancer-associated glycolipid antigens having complicated structures, and to generate monoclonal antibodies which can be used for the detection of naturally-occuring glycolipid antigens in human or animal cancer tissues. This combination of methods can be expected to considerably expand the realm of anticarbohydrate monoclonal antibodies. By this combination, it is possible to freely obtain monoclonal antibodies against very minor but valuable cancer-associated carbohydrate antigens, and even antibodies against artificially designed putative tumor associated antigens.

The antibodies according to the present invention are useful for detecting the presence of the cancer-associated lactoganglioseries glycolipid and will aid in diagnosis of cancers, including, for example, leukemia. Tests can be carried out by any of the well known methods in the art of immunological assays, such as ELISA, RIA, etc. Tissue samples, serum, urine, ascites, cerebrospinal fluid, hydrothorax and sperm can be used as samples to be assayed. Further, the monoclonal antibodies of this invention can be used in affinity chromatography to purify the bindable antigen. The monoclonal antibodies, labeled with a radioactive isotope, can be employed to detect or localize tumors, and at higher doses to therapeutically treat tumors. A chemotherapeutic agent can be attached to the monoclonal antibody to enhance its toxicity to cancer cells. Any species, such as humans and mice, which possesses the antigen can be subjected to treatment or diagnostic test employing the monoclonal antibodies of this invention.

The invention now being generally described, the same will be better understood by reference to certain specific examples which are included herein for purposes of illustration only and are not intended to be limiting of the invention or any embodiment thereof, unless specified.

Experimental Examples

Preparation of Glycolipids from Natural Sources

Neutral glycolipid mixtures from differentiated and undifferentiated M1 cells and human type O erythrocytes were prepared as described previously. See Kannagi, R. et al. Proc. Natl. Acad. Sci. USA 80, 2844–48, 1983; Kannagi, R. et al. J. Biol. Chem. 257, 14865–874, 1982; and Kannagi, R., J. Biol. Chem. 259 8444–451, 1984. The lactoganglioseries glycolipid in undifferentiated M1 cells was purified by high performance liquid chromatography followed by preparative TLC as described in Kannagi, R., J. Biol. Chem. 257, 14865–874, 1982. Amino CTH (Lc$_3$) was purified by the sequential degradation of sialylparagloboside purified from human erythrocytes by acid hydrolysis and β-galactosidase (from Jack Bean, Sigma, St. Louis, Mo.) treatment. Pure asialo GM$_2$ was obtained from murine cultured lymphoma cells L5178Y, by preparative TLC as described in Kannagi, R. et al., Cancer Res. 43, 4997–5005, 1983.

Synthons for the chemical synthesis of glycolipid

D-erythro-ceramide was synthesized from D-glucose as described in Koike, K. et al, Glycoconjugate J. 1, 107–109, 1985. Benzyl 2, 3, 6, 2', 6'-penta-O-benzyl-β-D-lactoside was prepared from lactose monohydrate (Kanto Chemical Co., Inc., Tokyo, Japan) as described in Ogawa, T. and Sugimoto, M., Carbohydrate Res., 135, C5–C9, 1985 and Litpak, A. et al., Carbohydrate Res. 52, 17–22, 1976. 3,4,6-Tri-O-acetyl-2-deoxy-2-phthalimido-β-D-galactopyranosyl bromide and 3,4,6-tri-O-acetyl-2-deoxy-2-phthalimido-β-D-galactopyranosyl bromide was prepared from D-galactose (Wako Pure Chemical Industries, Ltd., Osaka, Japan) and D-glucosamine hydrochloride (Tokyo Kasei Kogyo Co., Ltd., Tokyo, Japan), respectively, following the procedure in Lemieux, R.U. and Ratcliff, R. M., Can. J. Chem. 57, 1244–51, 1979. The overall sequences of steps for each synthon are given in FIGS. 2–6.

Monoclonal antibody procedures

The synthetic lactoganglioseries glycolipid was absorbed at the surface of acid-treated salmonella minnesota strain R595 and used for repeated intraperitoneal immunization of Balb/c mice. See Kannagi, R. and Hakomori, S. in "Handbook of Experimental Immunology, Vol. 4" ed. by Weir, D. M. and Herzenberg, L., Blackwell Scientific Pub. Inc., Boston, 1986, pages 117.1–117.20. The immunization protocol was 5 µg on day 4, 20 µg on day 7, 25 µg on day 12, and 35 µg on day 26 for the last boost. Three days later the spleen cells were harvested and fused with mouse myeloma P3/X63-Ag8U1(P3U1). The same synthetic glycolipid as used for immunization was used as the antigen in the solid-phase enzyme immunoassay of culture supernatants for the cloning procedures. Since one of the purposes of this study is to test the possibility or feasibility of using a chemically synthesized glycolipid as an immunogen to prepare monoclonal antibodies specific to a cancer antigen, throughout the course of preparation of the monoclonal antibody only synthetic glycolipid was used. Two representative clones secreting antibodies reactive with the synthetic glycolipid were chosen from 184 clones obtained in double fusions. The two clones, YI328-18 and YI328-51, were independently obtained and both secreted IgG$_3$ antibodies.

Assessment of the reactivity of monoclonal antibody with various glycolipids

The enzyme immunoassay was performed using various glycolipid antigens immobilized at the bottom of 96-well culture plates and peroxidase-conjugated goat anti-mouse IgG (heavy and light chain) by a standard method described by Hakomori, S. and Kannagi, R. in "Handbook of Experimental Immunology Vol. 1" ed. by Weir, D. M. and Herzenberg, L., Blackwell Scientific Pub. Inc., Boston, 1986. See also Kannagi, R., Stroup, R., Cochran, N. A., Urdal, D. L., Young, W. W. Jr. and Hakomori, S., Cancer Res. 43, 4997–5005, 1983. TLC-immunostaining was performed using a Baker HPTLC plate (Baker, Phillipsburg, N.J.) and $^{125}$Iprotein A as described first by Magnani, J. L. et al., Anal. Biochem. 109, 399–402, 1980, and subsequently modified (Kannagi R. et al., J. Biol. Chem. 257, 14865–874, 1982).

Outline of chemical synthesis of the lactoganglioseries glycolipid

The carbohydrate structures of the lactoganglioseries glycolipid and related glycolipid are shown in Table 1.

TABLE 1

CARBOHYDRATE STRUCTURES OF THE LACTOGANGLIOSERIES GLYCOLIPID AND RELATED GLYCOLIPIDS

| Glycolipid | Structure |
| --- | --- |
| 1. The lacto ganglioseries glycolipid (LcGg$_4$) | GalNAcβ1 →4<br>　　　　　　　Galβ1 →4Glcβ1 →1Cer<br>GlcNAcβ1 →3 |
| 2. Asialo GM$_2$ (Gg$_3$) | GalNAcβ1 →4Galβ1 →4Glcβ1 →1Cer |

TABLE 1-continued
CARBOHYDRATE STRUCTURES OF THE LACTOGANGLIOSERIES GLYCOLIPID AND RELATED GLYCOLIPIDS

| Glycolipid | Structure |
|---|---|
| 3. Amino CTH (Lc₃) | GlcNacβ1 ⟶ 3Galβ1 ⟶ 4Glcβ1 ⟶ 1Cer |
| 4. CDH (LacCer) | Galβ1 ⟶ 4Glcβ1 ⟶ 1Cer |

The lactoganglioseries glycolipid (LcGg₄) was synthesized in a stereo- and regio-controlled manner. The synthetic plan was designed based on the retrosynthetic analysis as shown in FIG. 1. The key glycosyl donor [2] was synthesized starting from benzyl 2, 3, 6, 2', 6'-penta-O-benzyl-β-D-lactoside [4]. 3-O-Benzoyl-D-erythroceramide [3] prepared from D-glucose was used as the glycosyl acceptor. 3,4,6-Tri-O-acetyl2-deoxy-2-phthalimido-β-D-glucopyranosyl bromide [5] and 3,4,6-tri-O-acetyl-2-deoxy-2-phthalimido-β-D-galactopyranosyl bromide [6] were used as hexosamine donors. For the control of regiochemistry, two hydroxyl groups of [4] were differentiated by taking advantage of a difference in their relative reactivity toward glycosylation. Stereochemical control of interglycosidic linkages is based on the 1,2-trans directing nature of phthalimido groups (Lemieux, R. U. et al., ACS Symp. Ser. 39, 90115, 1976) by using silver triflate for the reaction of [4] and [5], and silver silicate for the reaction of [4+5] and [6] and as the activating catalysts. See Paulsen, H., Ang. Chem. Int. Ed. 21, 155–173, 1982. At the final step of synthesis, structure [2] was reacted with protected ceramide [3] in the presence of silver perchlorate, stannous chloride and trimethylsilyl triflate. In total, 42 steps were necessary for the synthesis of the final product [1]. These steps are shown in FIGS. 2-6. The carbohydrate structure of the synthetic glycolipid was evident from the reaction sequence, and further supported by TLC and ¹H-NMR.

Specificity of the obtained monoclonal antibody as ascertained by TLC-immunostaining and solid phase enzyme immunoassay The specificity of the monoclonal antibodies produced by the established hybridomas, YI328-18 and YI328-51, was ascertained by the TLC-immunostaining technique. As shown in FIG. 7, both antibodies reacted equally well with either the synthetic lactoganglioseries glycolipid (lane 2 in FIG. 7a-d) or with the glycolipid purified from the natural source (lane 3 in FIGS. 7a and b), which is indicated by the strong staining of the glycolipid bands having the same TLC mobility in both lanes. Both antibodies recognized only the lactoganglioseries glycolipid in the neutral glycolipid mixture prepared from the undifferentiated M1 cell clone and were not reactive in asialo GM₂ present in the same preparation (Lane 6 in FIGS. 7a and b, lane 3 in FIGS. 7c and d). The reactivity of the antibodies with the highly related but nonbranched simple structures, pure amino CTH and asialo GM₂ (lanes 3 and 4 in FIGS. 7a and b), were almost negligible, while the control antibody 2D4 (Young, W. W. Jr. et al., J. Exp. Med. 150, 1008–1019, 1979) strongly reacted only with asialo GM₂ and not with the synthetic and natural lactoganglioseries glycolipid.

Similar results were obtained when the specificity was tested by solid-phase enzyme immunoassay (FIGS. 8a and b). Here again, YI328-18 and YI328-51 antibodies both reacted equally well with the synthetic lactoganglioseries glycolipid and the same glycolipid purified from M1 cells, the natural source. No significant cross-reactivity was observed with the related simple structures, asialo GM₂ and amino CTH, over the $2^7$ range.

Differentiation dependent change of the cancer-associated lactoganglioseries glycolipid as ascertained by the specific monoclonal antibody The TLC-immunostaining was performed on the glycolipid mixture prepared from either differentiated or undifferentiated M1 cells with the obtained specific monoclonal antibody YI328-18. As clearly shown in FIG. 9, the lactoganglioseries glycolipid in undifferentiated M1 cells (lane 2) shows strong staining as indicated by an arrow. This indicates that the glycolipid producing this band is the lactoganglioseries glycolipid, supporting the previous chemical findings (Kannagi, R. et al., J. Biol. Chem. 257, 14865–14874, 1982). On the other hand, the band having the same TLC mobility as the differentiated type cells (lane 3) was not stained by the antibody. This finding is compatible with the former chemical findings that the band is composed of paragloboside and not the lactoganglioseries glycolipid. Since the abnormal lactoganglioseries glycolipids have the identical TLC mobility as paragloboside, which is a common normal glycolipid, the detection and discrimination of this abnormal glycolipid is possible only with specific monoclonal antibodies such as YI328-18 or YI328-51.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A murine monoclonal antibody that specifically binds to an abnormal branched structure of a glycolipid antigen, wherein said antigen is a chemically synthesized lactoganglioseries glycolipid having the structure:

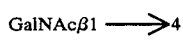
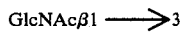

GalNAcβ1 ⟶ 4

Galβ1 ⟶ 4Glcβ1 ⟶ 1Cer

GlcNAcβ1 ⟶ 3 wherein said monoclonal antibody has 0% to 0.78% cross-reactivity with asialo GM₂ and amino CTH, and wherein said abnormal branched structure is a branched 1→3 connection.

2. The monoclonal antibody of claim 1, which is of the IgG₃ isotype.

3. The monoclonal antibody of claim 1, which is produced by a hybridoma formed by fusion of cells from a mouse myeloma line and spleen cells from a mouse previously immunized with a synthetic lactoganglioseries glycolipid having the structure:

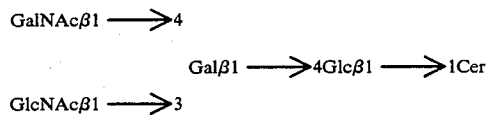

4. The monoclonal antibody of claim 1, which is produced by the hybridoma YI328-18.

5. The monoclonal antibody of claim 1, which is produced by the hybridoma YI328-51.

6. A hybridoma produced by the fusion of a murine lymphocyte with a murine myeloma, cell line that produces the antibodies of claim 1.

7. The hybridoma of claim 6, which produces antibodies of the IgG3 class.

8. The hybridoma of claim 6, which is YI328-18.

9. The hybridoma of claim 6, which is YI328-51.

10. A method of producing a monoclonal antibody according to claim 1, which comprises the steps of:
 (a) immunizing mice with said chemically synthesized glycolipid antigen;
 (b) removing the spleens from said mice and making a suspension of the spleen cells;
 (c) fusing said spleen cells with mouse myeloma cells in the presence of a fusion promoter;
 (d) diluting and separately culturing the fused cells in a medium which will only support growth of fused myeloma cells;
 (e) examining the medium from each of the separate cultures containing a hybridoma for the presence of antibodies which react with said glycolipid antigen;
 (f) selecting and cloning a hybridoma producing a monoclonal antibody which reacts with an abnormal branched structure of said glycolipid antigen, and which exhibits from 0% to 0.78% cross-reactivity with unbranched components of said antigen; and
 (g) recovering said monoclonal antibody.

* * * * *